(12) United States Patent
Ashraf

(10) Patent No.: US 10,182,812 B1
(45) Date of Patent: Jan. 22, 2019

(54) NEEDLE HOLDER

(71) Applicant: Aqeel J. A. GH. H. Ashraf, Safat (KW)

(72) Inventor: Aqeel J. A. GH. H. Ashraf, Safat (KW)

( * ) Notice: Subject to any disclaimer, the term of this patent is extended or adjusted under 35 U.S.C. 154(b) by 0 days.

(21) Appl. No.: 16/054,933

(22) Filed: Aug. 3, 2018

Related U.S. Application Data

(60) Provisional application No. 62/556,961, filed on Sep. 11, 2017.

(51) Int. Cl.
*A61B 17/062* (2006.01)
*A61B 17/04* (2006.01)

(52) U.S. Cl.
CPC ...... *A61B 17/062* (2013.01); *A61B 2017/047* (2013.01)

(58) Field of Classification Search
CPC ... A61B 17/0482; A61B 17/062; A61B 17/28; A61B 17/29; A61B 17/2909; A61B 2017/2901; A61B 2017/2902; A61B 2017/2903; A61B 2017/2909; A61B 2017/2912; A61B 2017/2913–2017/2915; A61B 2017/2923; A61B 2017/2927–2017/293
See application file for complete search history.

(56) References Cited

U.S. PATENT DOCUMENTS

| 3,168,097 | A |  | 2/1965 | Dormia |
| 5,282,806 | A | * | 2/1994 | Haber ................ A61B 17/29 606/139 |
| 5,643,294 | A |  | 7/1997 | Tovey et al. |
| 5,662,663 | A |  | 9/1997 | Shallman |
| 5,807,378 | A | * | 9/1998 | Jensen ................ B25J 3/04 606/1 |
| 2010/0016883 | A1 |  | 1/2010 | Christoudias |
| 2016/0302810 | A1 | * | 10/2016 | Whitney ........ A61B 17/00234 |
| 2017/0325903 | A1 | * | 11/2017 | Nichogi ............... A61B 17/00 |

FOREIGN PATENT DOCUMENTS

GB 872952 7/1961

* cited by examiner

*Primary Examiner* — Robert Lynch
*Assistant Examiner* — Lindsey Bachman
(74) *Attorney, Agent, or Firm* — Richard C. Litman

(57) ABSTRACT

The needle holder includes a primary hollow shaft, a secondary hollow shaft attached to the primary hollow shaft in a generally "T" configuration, a pair of extendible jaws rotatably positioned at a distal end of the primary shaft, a trigger mechanism mounted on the primary shaft for selectively extending the jaws, a first rotation member in the primary shaft, a second rotation member in the secondary shaft, a driven gear attached to the first rotation member, and a drive gear attached to the second rotation member and configured to selectively engage the first gear. The jaws are selectively extendible and rotatable.

9 Claims, 4 Drawing Sheets

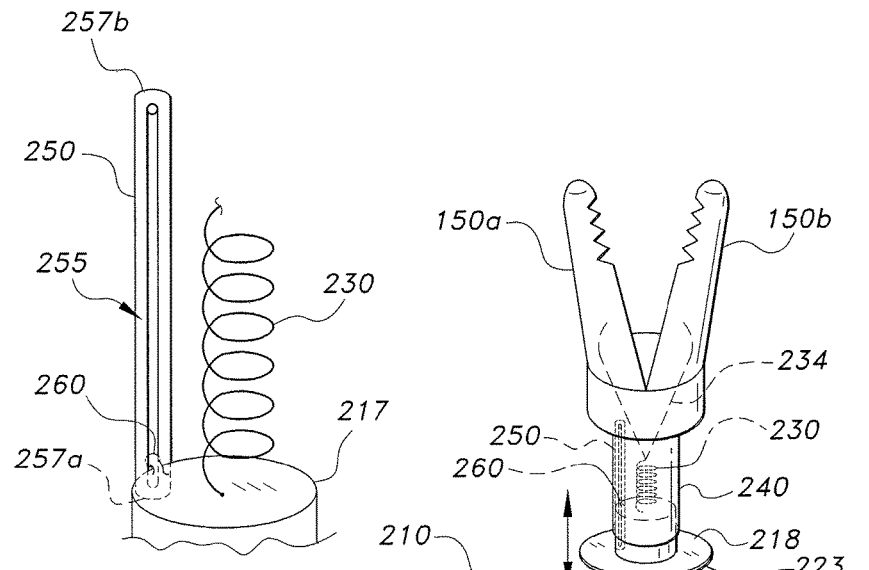
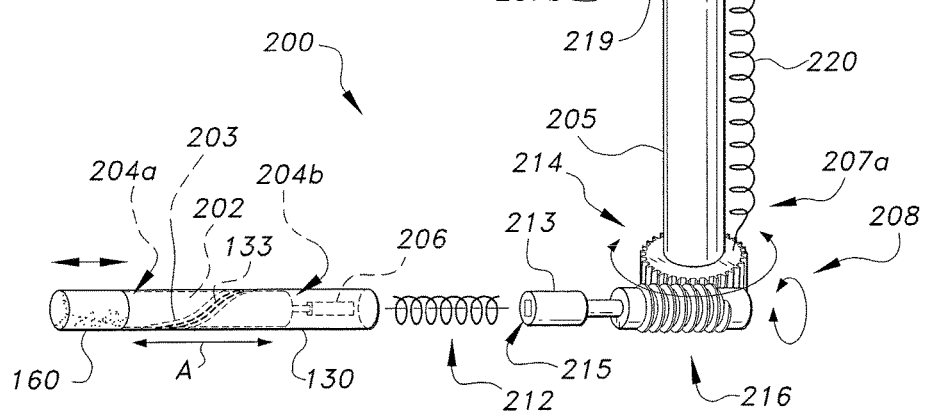
FIG. 2C
FIG. 2B

NEEDLE HOLDER

CROSS-REFERENCE TO RELATED APPLICATION

This application claims the benefit of U.S. Provisional Patent Application Ser. No. 62/556,961, filed Sep. 11, 2017.

BACKGROUND OF THE INVENTION

1. Field of the Invention

The present invention relates generally to surgical instruments, and particularly, to a needle holder capable of rotating a suture needle used in surgical stitching closure procedures.

2. Description of the Related Art

A needle holder is an essential tool in surgical procedures for the closure of skin and other tissue layers to achieve hemostasis and anastomosis. While minimal skills are required to use the needle holder, suturing wounds in areas with limited space and within deep structures may nevertheless become quite challenging. When stitching tissues, a surgeon generally has to pierce the tissue, rotate his/her wrist at least 180° for proper penetration of the needle into the tissue, dismount or remove the needle from the tissue and rotate the needle to point towards the tissue again to continue suturing. Suturing thick or deep tissue in this manner is particularly difficult with typical needle holders.

Thus, a needle holder solving the aforementioned problems is desired.

SUMMARY OF THE INVENTION

The needle holder includes a primary hollow shaft, a secondary hollow shaft attached to the primary hollow shaft in a generally "T" configuration, a pair of extendible jaws rotatably positioned at a distal end of the primary shaft, a trigger mechanism in communication with the primary shaft for selectively opening the jaws, a first rotation member in the primary shaft, a second rotation member in the secondary shaft, a first gear attached to the first rotation member, and a second gear attached to the second rotation member and configured to selectively engage the first gear. The jaws are selectively extendible and rotatable.

These and other features of the present disclosure will become readily apparent upon further review of the following specification and drawings.

BRIEF DESCRIPTION OF THE DRAWINGS

FIG. 2B is a perspective view showing the triggering mechanism of the needle holder wherein the jaws are in an open position and the worm drive, the primary hollow shaft being omitted to show the internal working mechanism.

FIG. 2C is an exploded view of a guide shaft of the needle holder.

Similar reference characters denote corresponding features consistently throughout the attached drawings.

DETAILED DESCRIPTION OF THE PREFERRED EMBODIMENTS

Figure 1:
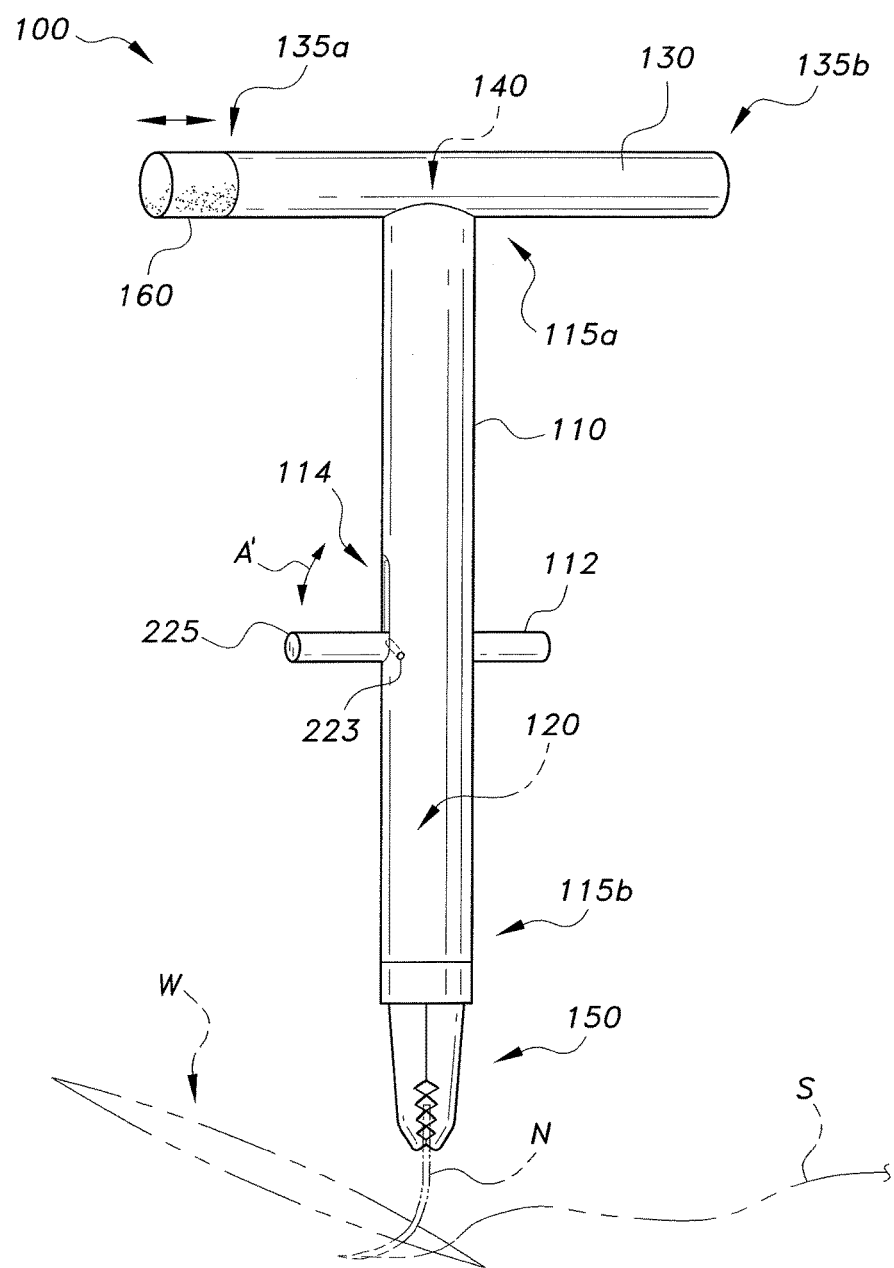
FIG. 1 is an environmental, perspective view of a needle holder having a pair of pivotal jaws.
Figure 2A:
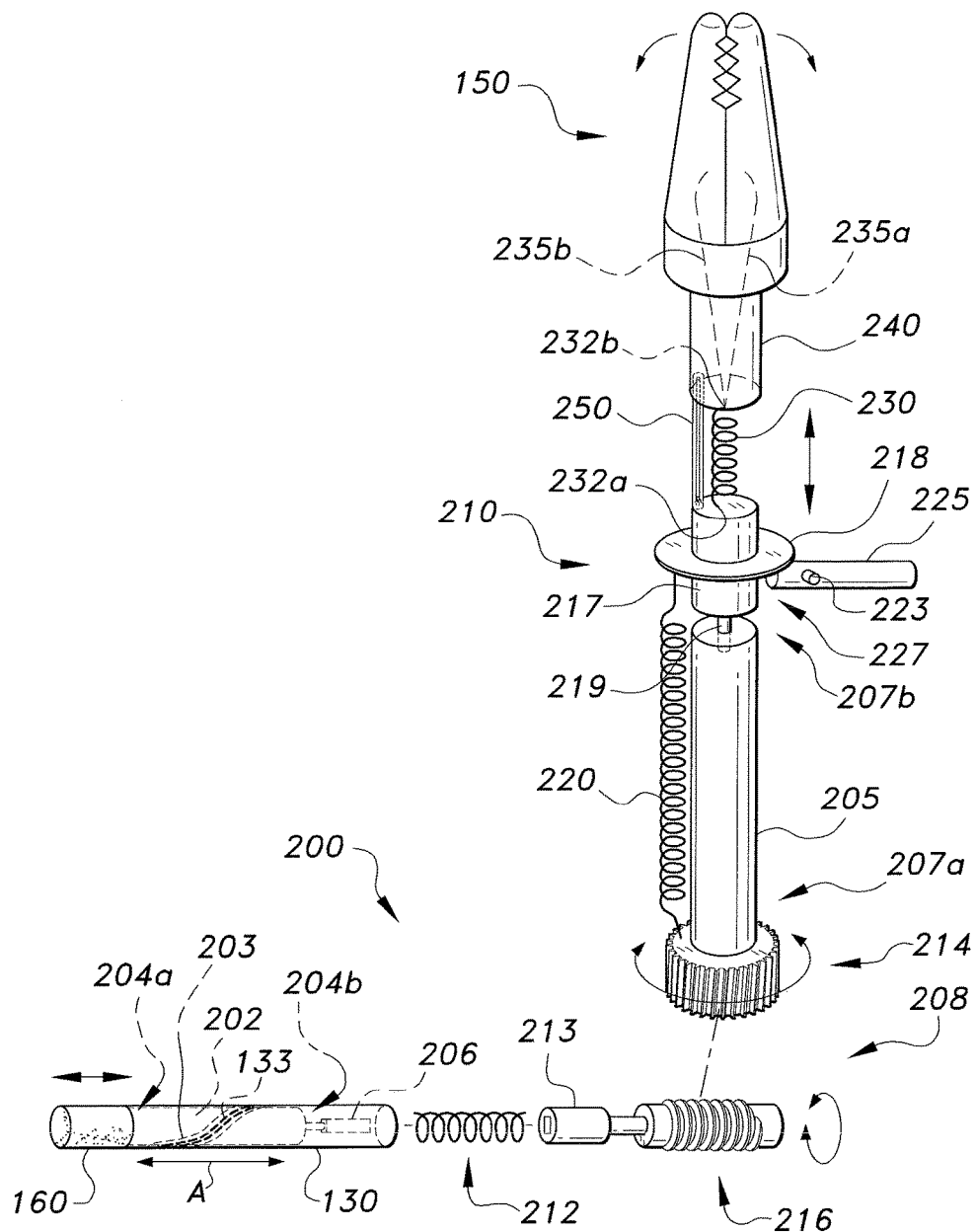
FIG. 2A is a perspective view showing a triggering mechanism of the needle holder wherein the jaws are in a closed position and an embodiment of a rotation apparatus including a worm drive, the primary hollow shaft being omitted to show the internal working mechanism.
Figure 3:
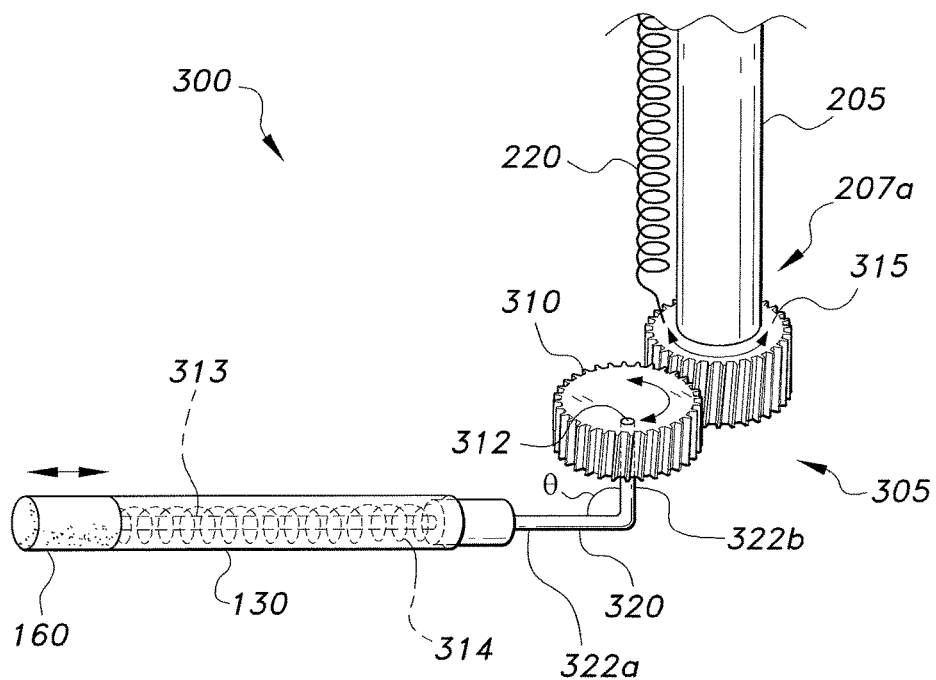
FIG. 3 is a partial perspective view showing an alternative embodiment of a rotating apparatus for the needle holder including a Hewland gear set instead of a worm drive, the primary hollow shaft being omitted to show the internal working mechanism.

Referring to FIGS. 1 through 3, the needle holder 100 includes a primary hollow shaft 110 and a secondary hollow shaft 130 attached to the primary hollow shaft 110 to form a frame having a generally "T" configuration, as illustrated in FIG. 1. The primary hollow shaft 110 includes a proximal end 115a, an opposing distal end 115b, and an interior channel 120 extending therethrough. The secondary hollow shaft 130 includes a first end 135a, an opposing second end 135b, and an interior channel 140 extending therethrough. The primary hollow shaft 110 may include at least one support bar 112 (FIG. 1) for additional support when using the needle holder 100. Both the primary hollow shaft 110 and the secondary hollow shaft 130 can be formed from any type of suitable medical grade material, such as stainless steel. Each hollow shaft 110, 130 can have any suitable configuration, such as a cylindrical configuration.

The needle holder 100 includes a trigger mechanism 210 to control movement of the jaws 150a and 150b for holding the surgical needle N attached to a suture S. The trigger mechanism 210 of the needle holder 100 includes a flexible pronged member 234 having prongs 235a and 235b, a trigger 225, and a pusher 217. The flexible pronged member 234, e.g., a V-shaped wire, includes a first prong 235a and a second prong 235b and extends at least partially within the primary hollow shaft 110 proximate the external jaws 150a, 150b. The member 234 can be partially supported within a tubular housing 240 in the primary hollow shaft 110. The pronged member 234 is resilient, naturally spreading apart when withdrawn from the tubular member 240, as shown in FIG. 2B, and being compressed together when withdrawn into the tubular member, as shown in FIG. 2A. The prongs 235a, 235b are attached to the inner face of the jaws 150a, 150b to pivot the jaws 150a, 150b open and closed, the resilient force being overcome by compression enough to grip a surgical needle N without slipping in the closed position. Preferably, the pronged member 234 is attached to a first spring or compressible member 230. The compressible member 230 extends between and connects the pronged member 234 and the pusher 217. The compressible member 230 is configured to provide a tension to hold the prongs 235a and 235b together in a first configuration and to release the tension on the prongs 235a and 235b in a second configuration. In the first configuration, the jaws 150a and 150b remain closed. In the second configuration, the jaws 150a and 150b are pushed open by the prongs 235a and 235b.

The trigger 225 is pivotally attached to the primary hollow shaft 110 by pivotal member 223. The pusher 217 includes a rotatable disc member 218 and a guide protrusion 260. One end of the trigger 225 is positioned in communicating relation with the disc member 218 and the other end of the trigger 225 extends outward through a slot 114 in the primary hollow shaft 110, as illustrated in FIG. 1. The guide protrusion 260 slidably engages a guide shaft 250 via channel 255. The pusher 217 extends between the first compressible member 230 and a second compressible member 220. The guide shaft 250 extends between the tubular housing and the pusher 217 and is attached to the tubular housing at end 257b.

In the first configuration, the jaws 150a and 150b are closed. When the trigger 225 is pulled by a user at one end, the disc member 218 is lifted by the other end of the trigger 225, causing the pusher 217 to slide up the guide shaft 250 and decrease the stress on the compressible member 230 and the prongs. As a result, the prongs extend away from each other and push open the jaws 150a and 150b. After the trigger 225 is released, the second compressible member 220 pulls the disc member 218 back to its original position.

Referring to FIGS. 2A and 2B, the needle holder 100 includes a rotation apparatus, generally designated as 200, positioned in communicating relation with the jaws 150a, 150b. The rotation apparatus 200 is configured for rotating the jaws 150a, 150b, such as approximately 180°, in a given direction, such as in a clockwise direction. The rotation apparatus 200 includes a first rotation member 205 positioned within the interior channel 120 of the primary hollow shaft 110 and a second rotation member 202 positioned within the interior channel 140 of the secondary hollow shaft 130. The first rotation member 205 includes a proximal end 207a and an opposing distal end 207b, the distal end 207b being operatively engaged with the jaws 150a, 150b. The second rotation member 202 includes a first end 204a connected to a push button or clicker 160, and an opposing second end 204b having a pusher 206. The pusher 206 can have any suitable shape, such as a generally triangular shape, a generally square shape, or a generally rectangular shape.

The secondary hollow shaft 130 and the second rotation member 202 can be threadably engaged. For example, the secondary hollow shaft 130 can include a ridge 133 extending in a spiral fashion along an inner surface thereof, such as from the first end 135a to the second end 135b. The second rotation member 202 can include a corresponding groove 203 extending along the outer surface of the second rotation member 202, such as from the first end 204a to the opposing second end 204b. The threaded connection facilitates rotation of the second rotation member 202 within the secondary hollow tube 130 in a given direction, such as in a clockwise or counter-clockwise direction when the clicker 160 is pushed by a user.

The rotation apparatus 200 may include a worm drive 208. The worm drive 208 includes a worm 216 and a worm gear 214. The worm 216 includes an extension member 213 protruding from an end thereof. The extension member 213 has an opening 215 configured for receiving pusher 206. For example, the pusher 206 may have a square shape and the opening 215 may have a corresponding square shape for receiving the pusher 206. A compressible member 212, such as a spring, extends between the second rotation member 202 and the extension member 213. The compressible member 212 is configured for returning the push button 160 back to its original (i.e., neutral) position once pressure exerted by a user has been released from the push button 160, as discussed further below.

By way of operation, when a user desires to rotate the jaws 150a, 150b s/he may depress the push button 160 to cause the rotation member 202 to rotate within the hollow shaft 130 towards the extension member 213, thereby pushing the compressible member 212. The pusher 206 moves into the opening 215 of the extension member 213, and the worm 216 is pushed against the worm gear 214. The pressure exerted on the extension member 213 of the worm 216 causes the worm 216 to engage with the worm gear 214 and simultaneously rotate the worm gear 214 in a given direction, such as in a counter-clockwise direction. The rotation of the worm gear 214 by the worm 216, in turn, rotates the first rotation member 205 and the corresponding jaws 150a, 150b approximately 180° in a given direction, such as in a counter-clockwise direction, about the longitudinal axis of the primary hollow shaft 110.

Once the jaws 150a, 150b are rotated, the user may release the push button 160, which, in turn, disengages the worm 214 from the worm gear 216 and allows the compressible member 212 to expand to push the second rotation member 202 back into its original position in the secondary hollow shaft 202.

FIG. 3 depicts another embodiment of a rotation apparatus, generally designated as 300, positioned in communicating relation with the jaws 150a, 150b. The rotation apparatus 300 includes a Hewland gear set 305 instead of the worm drive 208. Further, in the rotation apparatus 300, the secondary hollow shaft 130 does not include the inner ridge and the second rotation member 202 does not include the corresponding groove or a pusher.

Similar to the worm drive 208, the Hewland gear set 305 is configured for rotating the first rotation member 205 and the corresponding jaws 150a, 150b about the longitudinal axis of the primary hallow shaft 110. The Hewland gear set 305 includes a first spur gear 310 having a given diameter and a second spur gear 315 having a diameter greater than the diameter of the first gear 310. Like the worm gear 216, the second gear 315 is horizontally positioned on the proximal end 207a of the first rotation member 205. The Hewland gear set 305 further includes an L-shaped shaft 320 having a first end 322a, an opposing second end 322b, and an angled portion θ, e.g., a 90° angle, as illustrated in FIG. 3. An extension member 313 is coupled to the first end 322a of the shaft 320 and a compressible member 314 is positioned between extension member 313 and the second end 204b of the second rotation member 202. The first gear 310 includes an opening 312 configured for receiving the opposing second end 322b of the shaft 320.

By way of operation, once the push button 160 is depressed, the second end 204b of the second rotation member 202 compresses the compressible member 314 and pushes the shaft 320 and attached first gear 310 toward the second gear 315. Once the first gear 310 engages the second gear 315, the second gear 315 rotates. The movement of the shaft 320 causes the first gear 310 to rotate in a given direction, such as in a counter-clockwise direction, and in a given magnitude, such as 360°, which, in turn, causes the second gear 315 to rotate in a direction opposite the given direction, such as in a clockwise direction, and in a magnitude of approximately 180°. It is to be noted that since the first gear 310 has a smaller diameter than the second gear 315, when the first gear 310 is rotated 360° in a given direction, the second gear 315 may only rotate approximately 180°.

Similar to the rotation apparatus 200, the rotation of the first rotation member 205 by the second gear 315 rotates the jaws 150a, 150b in a direction and magnitude similar to the direction and magnitude of rotation of the first rotation member 205 about the longitudinal axis of the primary hallow shaft 110. Further, as with the rotation apparatus 200, once the jaws 150a, 150b are rotated, the pressure may then be released from the push button 160 causing the first gear 310 to disengage from the second gear 315. The compressible member 314 then expands to allow the second rotation member 202 to return to its original (i.e. neutral) position within the secondary hollow shaft 130.

It is to be understood that the needle holder is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A needle holder, comprising:
    a primary hollow shaft having a proximal end, an opposing distal end, and an interior channel extending therethrough;
    a secondary hollow shaft having a first end, an opposing second end, and an interior channel extending therethrough, the proximal end of the primary shaft being connected to a center portion of the secondary hollow shaft forming a T shape;
    a pair of extendable jaws rotatably positioned at the distal end of the primary hollow shaft, the jaws being adapted for selectively gripping a surgical needle;
    a trigger mechanism pivotally attached to the primary hollow shaft, the trigger mechanism being operatively connected to the jaws and imparting an opening force on the jaws when pushed by a user; and
    a push button located at one of the ends of the secondary hollow shaft;
    a driven gear connected to the extendable jaws and configured to rotate the extendable jaws by 180°; and
    a drive gear connectable to the driven gear, the drive gear being actuated by the push button to mesh with and selectively rotate the driven gear.

2. The needle holder according to claim 1, further comprising:
    a first rotation member attached to the driven gear, the first rotation member being positioned within the primary hollow shaft and being operatively engaged with the jaws;
    an extension member attached to the drive gear; and
    a second rotation member configured to engage the extension member, the second rotation member being positioned within the secondary hollow tube and engaged with the push button.

3. The needle holder according to claim 2, wherein said drive gear comprises a worm and said driven gear comprises a worm gear.

4. The needle holder according to claim 2, wherein:
    the drive and driven gears are engaged when the push button is in a pushed position; and
    the drive and driven gears are disengaged when the push button is in a neutral position.

5. The needle holder according to claim 2, wherein:
    the second rotation member engages the extension member when the push button is in a pushed position; and
    the second rotation member separates from the extension member when the push button is in a neutral position.

6. The needle holder according to claim 2, wherein:
    the interior channel of the second hollow shaft includes a helical ridge; and
    said second rotation member has a helical groove defined therein, the helical ridge engaging the helical groove to impart rotational movement to said second rotational member when said push button is activated.

7. The needle holder according to claim 1, further comprising:
    a first rotation member attached to the driven gear, the first rotation member being positioned within the primary hollow tube and being operatively engaged with the jaws; and
    an extension member, the extension member having a first end attached to the push button and a second end attached to the drive gear, the extension member being positioned within the secondary hollow tube.

8. The needle holder according to claim 1, wherein the trigger mechanism includes:
    a pronged member;
    a trigger; and
    a pusher in communication with the trigger and the pronged member, the pronged member selectively contacting the jaws to open and close the jaws.

9. The needle holder according to claim 8, further comprising a spring attached to the pronged member, the spring being configured to apply a tension to hold the prongs together in a closed configuration and to release the prongs in an open configuration.

* * * * *